United States Patent [19]
Burton et al.

[11] 3,993,758
[45] Nov. 23, 1976

[54] CEPHALOSPORIN COMPOUNDS

[75] Inventors: George Burton, Coulsdon; Elzbieta Watson, Carshalton, both of England

[73] Assignee: Beecham Group Limited, United Kingdom

[22] Filed: Jan. 15, 1975

[21] Appl. No.: 541,333

[30] Foreign Application Priority Data

Jan. 18, 1974 United Kingdom............... 2437/74
Apr. 10, 1974 United Kingdom............. 16059/74

[52] U.S. Cl. ............................ 424/246; 260/243 C
[51] Int. Cl.² ............... A61K 27/00; C07D 501/14

[58] Field of Search................ 260/243 C; 424/246

[56] References Cited
UNITED STATES PATENTS 3,516,997  6/1970  Takano et al. ................ 260/243 C
3,635,961  1/1972  Butler ........................... 260/243 C Primary Examiner—Nicholas S. Rizzo
Assistant Examiner—D. B. Springer

[57] ABSTRACT

A series of α-carboxy esters of cephalosporins having a 3-heterocyclicthio substituent which has been found active against many species of Gram-positive and Gram-negative organisms.

10 Claims, No Drawings

CEPHALOSPORIN COMPOUNDS

This invention relates to a series of cephalosporin derivatives, to methods for their preparation and to pharmaceutical compositions comprising them. Such compounds are antibacterially active against many species of Gram-positive and Gram-negative organisms.

According to the present invention there is provided a compound of formula (I):

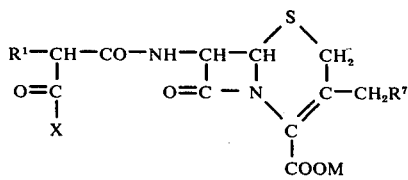

wherein $R^1$ is a phenyl, cyclohexa-1,4-dienyl, 4-hydroxyphenyl, 3,4-dihydroxyphenyl, 3-chloro-4-hydroxyphenyl, or 2- or 3-thienyl radical; $R^7$ is carbamoyloxy or $-SR^2$ wherein $R^2$ is a heterocyclic radical containing one or more of the atoms N, O and S or $R^2$ in an alkyl radical having from 1 to 3 carbon atoms; M is hydrogen, a pharmaceutically acceptable salt-forming ion, or a pivaloyloxymethyl, α-pivaloyloxyethyl, phthalidyl or 5,6-dimethoxyphthalidyl group; and X is $-OR^3$ or $-SR^4$ wherein $R^3$ is:
  phenyl
  substituted phenyl wherein the substituent is at least one of chloro, bromo, fluoro, lower alkyl, lower alkoxy, lower alkanoyl, carbo(lower) alkoxy, nitro or di(lower)-alkyl amino
  furyl
  quinolyl
  methylsubstituted quinolyl
  phenazinyl
  (1,3-benzodioxolyl)
  3-(2-methyl-4-pyronyl)
  3-(4-pyronyl) or
  N-(methylpyridyl);

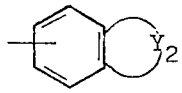

wherein $Y_2$ is
  $-CH=CH-O-$
  $-CH=CH-S-$
  $-CH_2-CH_2-S-$
  $-CH=N-CH=CH-$
  $-CH=CH-CH=CH-$
  $-C(O)-CH=CH-C(O)-$ or
  $-C(O)-C(O)-CH=CH-$;
or

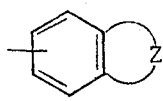

wherein Z is lower alkylene and is $(-CH_2)_3$ or $-(CH_2)_3-$, and substituted derivatives thereof wherein the substituent is methyl, chloro or bromo;
  benzyl or
  substituted benzyl wherein the substituent is chloro, bromo, fluoro, lower alkyl, lower alkoxy, lower alkanoyl, carbo(lower)alkoxy, nitro, or di(lower)alkylamino;
  phthalimidomethyl
  benzohydryl
  trityl
  cholesteryl
  alkenyl having up to 8 carbon atoms;
  alkenyl having up to 8 carbon atoms;
  (1-indanyl)methyl
  (2-indanyl)methyl
  furylmethyl
  pyridylmethyl
  (2-pyrrolidono)methyl
  (4-imidazolyl)methyl
  [2,2 - di(lower alkyl) - 1,3 - dioxolon - 4 - yl]methyl
  cycloalkyl and (lower alkyl) substituted cycloalkyl having from 3 to 7 carbon atoms in the cycloalkyl moiety
  bicyclo[4,4,0]decyl
  alkyl or substituted lower alkyl wherein the substituent is at least one of:
  chloro
  bromo
  fluoro
  nitro
  carbo (lower alkoxy)
  lower alkanoyl
  lower alkoxy
  cyano
  (lower)alkylmercapto
  (lower)alkylsulfinyl
  (lower)alkylsulfonyl
  ac-indanyl and substituted derivatives thereof wherein the substituent is methyl, chloro or bromo;
  ac-tetrahydronaphthyl and substituted derivatives thereof wherein the substituent is methyl, chloro or bromo;
  $-CH_2-CH_2-NR^5R^6$
  $-CH_2-CH_2-CH_2-NR^5R^6$
  $-CH_2-CH(CH_3)-NR^5R^6$ or
  $-CH(CH_3)-CH_2-NR^5R^6$
wherein $-NR^5R^6$ is $-NH$(lower alkanoyl),

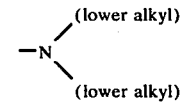

wherein the (lower alkyl) groups may be alike or different; $-N$(lower alkyl)anilino or substituted $-N$(lower alkyl)anilino wherein the substituent is chloro, bromo $-$(lower alkylene)$-Y_1$ wherein (lower alkylene) contains from 1 to 3 carbon atoms;
  and $Y_1$ is:
  azetidino
  aziridino
  pyrrolidino
  piperidino
  morpholino
  thiomorpholino
  N-(lower alkyl)piperazino pyrrolo
imidazolo
2-imidazolino
2,5-dimethylpyrrolidino
1,4,5,6-tetrahydropyrimidino
4-methylpiperidino or
2,6-dimethylpiperidino;
and R⁴ is a phenyl or mono-, di-, or tri-substituted phenyl wherein the substituent is at least one of chloro, bromo, fluoro, lower alkyl, lower alkoxy, or trifluromethyl.

In the compounds of formula (I) above, R¹ is preferably 3-thienyl, R² is preferably methyl or a group of formula (II) or (III):

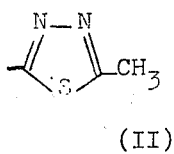   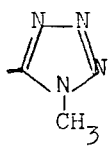

(II)   (III)

and X is preferably phenoxy or 5-indanyloxy and M is hydrogen or a pharmaceutically acceptable salt-forming ion.

In general the presence of the group R⁷ in compounds of formula (I) above, gives them therapeutic advantages over compounds of somewhat similar structure (disclosed in British Patent Specification No. 1,243,206) wherein in place of the group R⁷ there is a hydrogen atom, a hydroxy, acetoxy or tertiary amino group.

One particularly valuable compound of this invention is 7-(α-phenoxy carbonylthien-3-ylacetamido)-3-(1'-methyl-1'H-tetrazol-5'-ylthio)methylceph-3-em-4-carboxylic acid (and its pharmaceutically acceptable salts) which is highly active against a wide range of gram-positive and gram-negative organisms, especially strains of *E.coli, Klebsiella SPP, Enterobacter cloacae, Enterobacter aerogenes, Proteus mirabilis, Proteus morganii,* and *Proteus rettgerii* normally resistant to cephalosporins. Significant activity against such normally resistant organisms is also found with other compounds of this invention, including the 3-(2'-methyl-1',3',4'-thiadiazol-5'-ylthio)methyl and 7-(α-phenoxycabonyl-phenylacetamido) analogues of the above compound.

The compounds of formula (I) wherein R⁷ is —SR² can be prepared by reacting a compound of formula (IV):

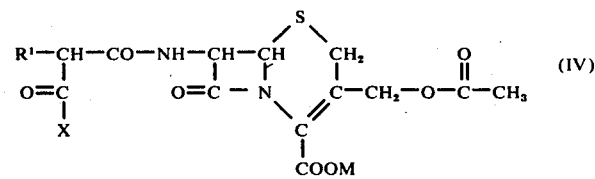

wherein R¹, X and M are as defined for formula (I) and wherein any reactive groups may be blocked with a thiol of formula HS—R² wherein R² is as defined for formula (I) above, and thereafter, if necessary, the following steps are carried out:

i. removal of any blocking groups in the acyl side chain.

ii. conversion of one group M to a different group M.

To prepare compounds of formula (I) wherein R⁷ is carbamoyloxy or —SR², a compound of formula (V):

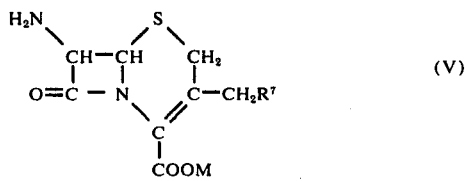

wherein M is as defined for formula (I) above may be reacted with a reactive N-acylating derivative of an acid of formula (VI):

or with a ketene compound of formula (VII):

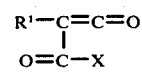

wherein R¹ and X are as defined in formula (I) and wherein any reactive groups, such as amino and hydroxy groups may be blocked, and thereafter, if necessary carrying out the following steps:

i. removal of any blocking groups in the acyl side chain;

ii. conversion of one group M to a different group M.

A reactive N-acylating derivative of the acid (VI) is employed in the above process. The choice of reactive derivative will of course be influenced by the chemical nature of the substituents in the acid. Thus, when the acid contains only acid stable groups, an acid halide is a suitable N-acylating derivative, preferably the acid chloride.

Such reagents, would, however, be avoided when an acid labile group was present in the acid (VI). In such cases a suitable N-acylating derivative is a mixed anhydride. For this purpose particularly convenient mixed anhydrides are the alkoxyformic anhydrides.

Alternative N-acylating derivatives of acid (VI), are activated esters. Such activated esters, for example the ester formed with 1-hydroxybenztriazole or N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (VI) include the reactive intermediate formed by reaction in situ with a carbodiimide or carbonyldiimidazole, but the literature on the preparation of semi-synthetic penicillins contains examples of other reactive N-acylating derivatives of acids suitable for coupling to 6-APA, for example the acid azide.

It will be understood, of course, that where a free acid of type (I) or salt thereof is desired, it may be convenient to carry out the acylation reaction using an ester of (V) and then to remove the ester group. Vice versa, if an ester is required, it may be convenient to carry out the acylation reaction using compound (V) wherein M is hydrogen or a salt forming ion and thereafter to esterify the free acid.

In the above process, if it is necessary to block any reactive substituents in the acid (VI), conventional chemical blocking groups are known. Thus, if desired, any free amino groups may be blocked by conversion to t-butyloxycarbonyl or benzyloxycarbonylamino groups, or the amino group may be blocked as the nitro group which is later converted to the amino group.

The compounds of formula (I) wherein $R^7$ is a carbamoyloxy group may also be prepared from the corresponding 3-hydroxymethyl compound by carbamoylation of the hydroxy group. In such a process a compound of formula (VIII):

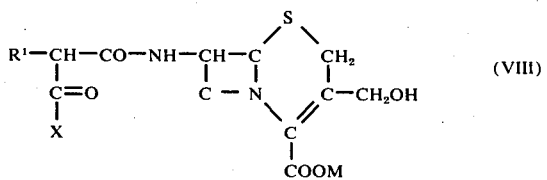

(VIII)

wherein $R^1$, X and M are as defined in formula (I), and wherein any reactive groups may be blocked, is reacted with an isocyanate of formula $R^8NCO$ where $R^8$ is a group which is removable from the reaction product with compound (VIII) under mild conditions to give compound (I) and, thereafter, if necessary, the following steps are carried out:

i. removal of any blocking groups in the acyl side chain;

ii. conversion of one group M to a different group M.

The intermediates of formula (VIII) may be prepared by the action of an esterase, for example, citrus acetyl esterase, on the corresponding compound of formula (I), wherein $R^7$ is an acetoxy group.

The following Examples illustrate the preparation of some of the compounds of this invention:

EXAMPLE 1

Sodium 7-(α-Phenoxycarbonylthien-3-ylacetamido)-3-(2'-methyl-1',3',4'-thiadiazol-5'-ylthio)methylceph-3-em-4-carboxylate α-(Phenoxycarbonyl)thien-3-ylacetyl chloride (0.01M) in anhydrous acetone (25ml.) was added to an ice bath cooled solution of 7-amino-3-(2'-methyl-1',-3',4'-thiadiazol-5'-ylthio)methylceph-3-em-4-carboxylic acid (0.01M) and triethylamine (3.0ml.) in acetone (25ml.) and water (50ml.). The solution was stirred at room temperature for 3 hours, the acetone was removed in vacuo and the aqueous residue was diluted with water. The aqueous solution was covered with ethyl acetate (50ml.), acidified to pH 1.5 with 1N HCl, the organic phase was separated off and the aqueous layer extracted with ethyl acetate (50ml.). The combined extracts were washed with water (2 × 50ml.) and brine (50ml.) and brine (50ml.), dried over anhydrous magnesium sulphate, treated with 2N sodium 2-ethylhexoate in methyl isobutyl ketone (1.5ml.) and diluted with anhydrous ether (100ml.). The precipitated sodium salt was collected, washed with anhydrous ether and dried in vacuo.

Yield 29.5%; N.m.r. spectrum $[(CD_3)_2SO]\delta = 9.8–9.4$ (1H,m, —NH—), 7.7–7.0 (8H,m, aromatic and thienyl protons), 5.8–5.3 (1H,m, $C_7$ proton), 5.40 (1H,s, α-proton), 5.2–4.9 (1H,m, $C_6$ proton), 4.8–4.0 (2H,M, —$CH_2S$—), 4.0–3.1 (2H,m, $C_2$ methylene protons), 2.67 (3H,m, thiadiazole methyl protons); u.v. spectrum (95% ethanol), λmax. 274nm (ε = 14.640). Paper chromatography showed a zone at $R_f$=0.67.

EXAMPLE 2

Sodium 7-(α-phenoxycarbonylthien-3-ylacetamido)-3-(1'-methyl-1'H-tetrazol-5'-ylthio)methylceph-3-em-4-carboxylate α-(Phenoxycarbonyl)thien-3-ylacetyl chloride was reacted with 7-amino-3-(1'-methyl-1'H-tetrazol-5'-ylthio)methylceph-3-em-4-carboxylic acid as described in Example 1.

Yield 22.1%; N.m.r. spectrum $[(CD_3)_2SO]$, δ=9.8–9.5 (1H,m, —NH—), 7.7–7.0 (8H,m, aromatic and thienyl protons), 5.8–5.3 (1H,m, $C_7$ proton), 5.40 (1H,s, α-proton), 5.2–4.9 (1H,m, $C_6$ proton), 4.7–4.1 (2H,m, —$CH_2S$—), 3.95 (3H,s, tetrazole methyl protons), 4.0–3.1. (2H,m, $C_2$ methylene protons); u.v. spectrum (95% ethanol), λmax. 268nm (ε =9,700). Paper chromatography showed a zone at $R_f$=0.59.

EXAMPLE 3

Sodium 7-(α-methoxycarbonylthien-3-ylacetamido)-3-(1'-methyl-1'H-tetrazol-5'-ylthio)methylceph-3-em-4-carboxylate α-(Methoxycarbonyl)thien-3-ylacetyl chloride was coupled with 7-amino-3-(1'-methyl-1'H-tetrazol-5'-ylthiol)methylceph-3-em-4-carboxylic acid in aqueous acetone as described in Example 1.

Yield 40.7%; N.m.r. spectrum $[(CD_3)_2SO]$,δ=9-.3–9.0 (1H,m, —NH—), 7.6–7.0 (3H,m, thienyl protons), 5.7–5.4 (1H,m, $C_7$ proton), 5.10 (1H,s, α-proton), 5.1–4.8 (1H,s, $C_6$ proton), 4.7–4.1 (2H,m, —$CH_2S$—), 3.95 (3H,s, tetrazole —$CH_3$), 3.70 (3H,s, —$CO_2CH_3$), 3.8–3.2 (2H,m, $C_2$ methylene protons); u.v. spectrum (95% ethanol), λmax. 272nm (ε=7,800). Paper chromatography showed a zone at $R_f$ = 0.55.

EXAMPLE 4

Sodium 7-(α-phenoxycarbonylphenylacetamido)-3-(1'-methyl-1'H-tetrazol-5'-ylthio)methylceph-3-em-4-carboxylate α-(Phenoxycarbonyl)phenylacetyl chloride was reacted with 7-amino-3-(1'-methyl-1'H-tetrazol-5'-ylthio)methylceph-3-em-4-carboxylic acid as described in Example 1.

Yield 35.7%; n.m.r. spectrum $[(CD_3)_2SO]$, δ=9.8–9.4 (1H,m, —NH—), 7.7–7.1 (10H,m, aromatic protons), 5.8–5.4 (1H,m, $C_7$ proton), 5.28 (1H,s, α-proton), 5.2–4.8 (1H,m, $C_6$ proton). 4.6–4.2 (2H,m, —$CH_2S$—), 3.92 (3H,s, —$CH_3$), 3.8–3.2 (2H,m, $C_2$ methylene protons); u.v. spectrum (95% ethanol), λmax. 270nm (ε=10,700). Paper chromatography showed one zone, $R_f$=0.58.

EXAMPLE 5

Sodium 7-(α-benzyloxycarbonylthien-3-ylacetamido)-3-(1'-methyl-1'H-tetrazol-5'-ylthio)methylceph-3-em-4-carboxylate α-(Benzyloxycarbonyl)thien-3-ylacetyl chloride was converted to the cephalosporin by the technique described in the previous examples.

Yield 24.9%; n.m.r. spectrum [(CD$_3$)$_2$SO],δ=9.5–9.2 (1H,m, —NH—), 7.3–7.0 (8H,m, aromatic and thienyl protons), 5.7–5.4 (1H,m, C$_2$ proton), 5.15 (3H,s, —OCH$_2$Ph and α-proton), 5.3–4.9 (1H,m, C$_6$ proton), 4.7–4.1 (2H,m, —CH$_2$S—), 3.95 (3H,s, —CH$_3$), 3.8–3.1 (2H,m, C$_2$ methylene protons); u.v. spectrum (95% ethanol, λmax. 270nm (ε=7,415). Paper chromatography showed a zone at R$_f$=0.50

EXAMPLE 6

7-(α-Phenoxycarbonylthien-3-ylacetamido)-3-(1'H-1',2',4'-triazol-3'-ylthio)methylceph-3-em-4-carboxylic acid 7-amino-3-(1'H-1',2',4'-triazol-3'-ylthio)methyl-ceph-3-em-4-carboxylic acid (1.45g., 4.6 mmole) was suspended in anhydrous dichloromethane (15ml.) containing pyridine (1.26ml., 10.4 mmole) and N,O-bis-trimethylsilylacetamide (1.86ml., 10.4 mmole) an stirred at room temperature for 1 hour. Further N,O-bistrimethylsilylacetamide (1.0ml.) was added and the mixture stirred for 30 minutes then cooled in an ice bath and treated dropwise with a solution of αphenoxycarbonylthien-3-yl-acetyl chloride (5.0 mmole) in dichloromethane (15ml.). The solution was stirred at room temperature for three hours then evaporated to dryness in vacuo and the residue dissolved in ethyl acetate (50ml.) and water (50ml.). The ethyl acetate was discarded, the aqueous solution was covered with ethyl acetate (25ml.), acidified to pH 1.5 with N-hydrochloric acid, the organic layer was collected and the aqueous phase extracted with more ethyl acetate (25ml.). The combined extracts were washed with water (50ml.) and saturated brine (25ml.), dried over anhydrous magnesium sulphate, evaporated to dryness in vacuo and the residue triturated with anhydrous ether to give the cephalosporin free acid as a buff coloured solid.

Yield 1.28, 46.1A; n.m.r. spectrum [(CD$_3$)$_2$SO], δ=8.7–8.3 (1H,m, —NH—), 8.53 (1H,s, triazole —CH—), 8.1–7.0 (8H,m, aromatic and thienyl protons), 6.1–5.7 (1H,m, C$_7$ proton), 5.38 (1H,s, α-proton, 5.3–5.1 (1H,m, C$_6$ proton), 4.30 (2H,s, —CH$_2$S—), 4.0–3.5 (2H,m, C$_2$ methylene protons); U.V. spectrum (95% ethanol), λmax. 269nm (ε=7,940).

What we claim is:
1. A compound of formula (I):

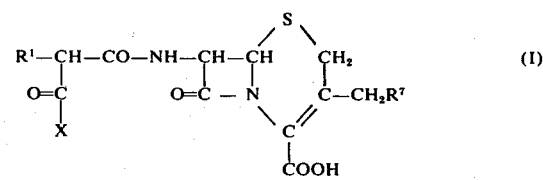

wherein R$^1$ phenyl, cyclohexa-1,4-dienyl, 4-hydroxyphenyl, 3,4-dihydroxyphenyl, 3-chloro-4-hydroxyphenyl or 2- or 3-thienyl; R$^7$ is carbamoyloxy 2-methyl-1,3,4-thiadiazol-5-yl thio, 1-methyl-1H-tetrazol-5-yl thio, 1H-1,2,4-triazol-3-yl thio or an alkylthio radical having from 1 to 3 carbon atoms; X is phenoxy, methoxy, or benzyloxy; or a pharmaceutically acceptable slt or a pivaloyloxymethyl, α-pivaloyloxyethyl, phthalidyl or 5,6-dimethoxyphthalidyl ester thereof.

2. A compound as in claim 1 wherein R$^1$ is 3-thienyl; R$^7$ is methylthio or a group of formula (II) or (III):

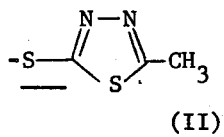 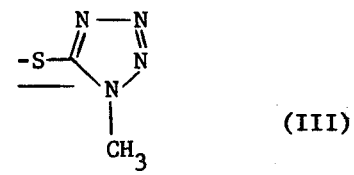

X is phenoxy, or a pharmaceutically acceptable salt thereof.

3. 7-(α-phenoxycarbonylthien-3-ylacetamido)-3-(1'-methyl-1'H-tetrazol-5'-ylthio)methylceph-3-em-4-carboxylic acid or a pharmaceutically acceptable salt thereof.

4. 7-(α-phenoxycarbonylthien-3-ylacetamido)-3-(2'-methyl-1',3',4'-thiadiazol-5'-ylthio)methylceph-3-em-4-caboxylic acid or a pharmaceutically acceptable salt thereof.

5. 7-(α-Methoxycarbonylthien-3-ylacetamido)-3-(1'-methyl-1'H-tetrazol-5'-ylthio)methylceph-3-em-4-caboxylic acid or a pharmaceutically acceptable salt thereof.

6. 7-(α-Phenoxycarbonylphenylacetamido)-3-(1'-methyl-1'H-tetrazol-5'-ylthio)methylceph-3-em-4-carboxylic acid or a pharmaceuticallly acceptable salt thereof.

7. 7-(α-benzyloxycarbonylthien-3-ylacetamido)-3-(1'-methyl-1'H-tetrazol-5'-ylthio)methylceph-3-em-a-carboxylic acid or a pharmaceutically acceptable salt thereof.

8. 7-(α-Phenoxycarbonylthien-3-ylacetamido)-3-(1'H-1',2',4'-triazol-3'-ylthio)methylceph-3-em-4-caboxylic acid or a pharmaceutically acceptable salt thereof.

9. An antibacterial pharmaceutical composition which comprises an effective amount of a compound of claim 1, together with a pharmaceutically acceptable carrier.

10. A composition as claimed in claim 9 in unit dosage form.

* * * * *